(12) United States Patent
Porter

(10) Patent No.: US 6,921,410 B2
(45) Date of Patent: Jul. 26, 2005

(54) INJECTION MOLDED VASO-OCCLUSIVE ELEMENTS

(75) Inventor: Stephen Christopher Porter, Fremont, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 382 days.

(21) Appl. No.: 09/866,892

(22) Filed: May 29, 2001

(65) Prior Publication Data

US 2002/0193819 A1 Dec. 19, 2002

(51) Int. Cl.[7] ............................................. A61M 29/00
(52) U.S. Cl. ............................................. 606/191
(58) Field of Search .................. 606/158, 191, 606/192, 194, 195, 200, 198, 213, 215; 59/78, 80, 82, 84, 85; 623/1.11, 1.15, 1.45, 1.46, 1.49, 1.16, 1.23, 1.34, 1.39, 1.42, 1.54, 901, 903

(56) References Cited

U.S. PATENT DOCUMENTS

| | | | | |
|---|---|---|---|---|
| 3,913,183 A | * | 10/1975 | Brumlik ........................ | 24/447 |
| 4,994,069 A | | 2/1991 | Ritchart et al. | |
| 5,122,136 A | | 6/1992 | Guglielmi et al. | |
| 5,341,634 A | * | 8/1994 | Straight ........................ | 59/80 |
| 5,354,295 A | | 10/1994 | Guglielmi et al. | |
| 5,395,333 A | * | 3/1995 | Brill ........................ | 604/101.05 |
| 5,690,666 A | | 11/1997 | Berenstein et al. | |
| 5,703,200 A | * | 12/1997 | Bezwada et al. ........... | 528/354 |
| 5,826,587 A | | 10/1998 | Berenstein et al. | |
| 5,853,418 A | * | 12/1998 | Ken et al. ................... | 606/191 |
| 5,925,059 A | * | 7/1999 | Palermo et al. ............. | 606/191 |
| 6,024,754 A | * | 2/2000 | Engelson ..................... | 606/213 |
| 6,063,111 A | * | 5/2000 | Hieshima et al. .......... | 606/191 |
| 6,171,338 B1 | * | 1/2001 | Talja et al. ................. | 623/1.22 |
| 6,200,335 B1 | * | 3/2001 | Igaki .......................... | 623/1.15 |
| 6,221,091 B1 | * | 4/2001 | Khosravi ..................... | 606/200 |
| 6,261,305 B1 | * | 7/2001 | Marotta et al. ............. | 606/200 |
| 6,280,457 B1 | * | 8/2001 | Wallace et al. ............. | 606/200 |
| 6,293,960 B1 | * | 9/2001 | Ken ............................. | 606/195 |
| 6,309,367 B1 | * | 10/2001 | Boock ......................... | 602/1 |
| 6,332,884 B1 | * | 12/2001 | Cooper ........................ | 606/77 |
| 6,375,668 B1 | * | 4/2002 | Gifford et al. .............. | 606/200 |
| 6,423,818 B1 | * | 7/2002 | Matsuda et al. ............ | 528/354 |
| 6,458,127 B1 | * | 10/2002 | Truckai et al. ............. | 606/49 |
| 6,547,804 B2 | * | 4/2003 | Porter et al. ............... | 606/195 |
| 6,585,754 B2 | * | 7/2003 | Wallace et al. ............. | 623/1.15 |
| 6,596,012 B2 | * | 7/2003 | Akerfeldt et al. .......... | 606/213 |
| 6,613,074 B1 | * | 9/2003 | Mitelberg et al. .......... | 623/1.11 |
| 6,632,503 B1 | * | 10/2003 | Shikinami et al. ......... | 428/131 |
| 6,656,173 B1 | * | 12/2003 | Palermo ...................... | 606/32 |
| 2002/0016596 A1 | * | 2/2002 | Cooper ........................ | 606/77 |
| 2003/0206928 A1 | * | 11/2003 | Tormala et al. ............ | 424/400 |

OTHER PUBLICATIONS

Dondlinger et al.,Embolization Materials ed., *Interventional Radiology*, Thieme, N.Y. 295–313 (1990).

Herrera et al., "Histological Changes in the Rat Common Carotid Artery Induced by Aneurysmal Wrapping and Coating Materials," Neurol. Med. Chir (Tokyo) 39(2):134–139 (1999).

Moringlane et al.,"Experimental Aneurysms in the Rabbit: Occlusion by Intrasaccular Injection of Fibrin Sealant," *Surg Neurol*. 28(5):361–366 (1987).

(Continued)

*Primary Examiner*—Ismael Izaguirre
(74) *Attorney, Agent, or Firm*—Robins & Pasternak LLP

(57) ABSTRACT

Compositions comprising injection-molded vaso-occlusive elements are described. Thus, one or more injection-molded elements are formed into a desired three-dimensional configuration. Each injection-molded element of the device may have a different shape, for example, ovoid, spherical, cylindral or pyramidal. The devices described herein may also be detachable linked to pusher element for placement in a body cavity. Also described are methods of making and using these elements.

48 Claims, 4 Drawing Sheets

OTHER PUBLICATIONS

Moringlane et al., "Occlusion of Experimental Artery Aneurysms by Intrasaccular Injection of Fibrin Sealant," *Acta Neurochir Suppl.* (*Wein*) 43:193–197 (1988).

Suga et al., "Fibrin Glue, Aneurysmal Occlusion, Angioplastic Ballon," *No Shinkei Geka* 20(8):865–873 (1992).

Vinters et al., "The Histotoxicity of Cyanoacrylates," *Neuroradiology* 27:279–291 (1995).

* cited by examiner

INJECTION MOLDED VASO-OCCLUSIVE ELEMENTS

FIELD OF THE INVENTION

Compositions and methods for repair of aneurysms are described. In particular, injection-molded polymeric vaso-occlusive devices are disclosed, as are methods of making and using these devices.

BACKGROUND

An aneurysm is a dilation of a blood vessel (similar to a balloon) that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. (See, e.g., U.S. Pat. No. 4,994,069 to Ritchart et al.) Other less stiff helically coiled devices have been described, as well as those involving woven braids.

U.S. Pat. No. 5,354,295 and its parent, U.S. Pat. No. 5,122,136, both to Guglielmi et al., describe an electrolytically detachable embolic device. Vaso-occlusive coils having little or no inherent secondary shape have also been described. For instance, co-owned U.S. Pat. Nos. 5,690,666 and 5,826,587 by Berenstein et al., describes coils having little or no shape after introduction into the vascular space.

Liquid embolics, such as cyanoacrylate glues and fibrin sealants, have also been used in animal and human subjects. See, e.g., Interventional Radiology, Dandlinger et al, ed., Thieme, N.Y., 1990:295–313; Suga et al. (1992) *No Shinkei Geka* 20(8):865–873; Moringlane et al. (1987) *Surg Neurol* 28(5):361–366; Moringlane et al. (1988) *Acta Neurochir Suppl.* (*Wein*) 43:193–197. Of these liquid embolics, cyanoacrylate glues are the only liquid embolics currently available to neurosurgeons. However, chronic inflammation is typically seen with cyanoacrylate treatments (Herrera et al. (1999) *Neurol Med Chir* (Tokyo) 39(2):134–139) and the degradation product, formaldehyde, is highly toxic to the neighboring tissues. See, Vinters et al (1995) *Neuroradiology* 27:279–291. Another disadvantage of cyanoacrylate materials is that the polymer will adhere both to the blood vessel and to the tip of the catheter. Thus physicians must retract the catheter immediately after injection of the cyanoacrylate embolic material or risk adhesion of the cyanoacrylate and the catheter to the vessel.

None of these documents describe injection molded vascular occlusion elements having the characteristics described herein or methods of making and using such devices.

SUMMARY OF THE INVENTION

Thus, this invention includes novel occlusive compositions as well as methods of using and making these compositions.

In one aspect, the invention includes a method for producing a vaso-occlusive element comprising the step of injection molding a polymeric material into the three-dimensional configuration. In preferred embodiments, the polymeric material is absorbable, for example, polyglycolide, poly-L-lactide, poly(g-ethyl glutamates), polyphosphazene, polysaccharides, polyorthoesters, polycaprolactone, polyhydroxybutyrate, polydioxanone, polycarbonates, polyanhydrides, copolymers or blends thereof, collagen, elastin, fibrinogen, fibronectin, vitronectin, laminin, gelatin and combinations thereof. The three-dimensional configuration can be any shape, for example, a cylindrical configuration having a longitudinal axis or a plurality of shaped structures (e.g., ovals, spheres, cones, pyramids, blocks or combinations of these shapes) linked in series.

In any of the methods described herein, the three-dimensional configuration can prepared as a single-molded element or, alternatively, can be formed by linking two or more discrete elements. When formed by linking multiple elements, the linking element can be, for example a polymeric wire or a ductile metallic wire. The three-dimensional configuration can further include additional modifications, for example a cylindrical device may be produced with a plurality of channels therein (e.g; channels perpendicular to the longitudinal axis of the device).

In certain embodiments, any of the methods described herein further comprise the step of providing, on the injection molded element, a severable junction detachably connected to a pusher element. In certain embodiments, the severable junction(s) are, an electrolytically detachable assembly adapted to detach by imposition of a current on said pusher element; a mechanically detachable assembly adapted to detach by movement or pressure imposed on or within said pusher element; a thermally detachable assembly adapted to detach by localized delivery of heat to said junction; a radiation detachable assembly adapted to detach by delivery of electromagnetic radiation to said junction or combinations thereof.

Any of the methods described herein can further comprise additional production steps, for instance, micro-machining the injection-molded element; chemically etching the injection-molded element; laser cutting the injection-molded element; and linking a plurality of injection-molded elements together (e.g., by soldering, interference fitting, friction fitting, stringing, ultrasonic welding, thermal welding and solvent bonding). More than one additional production steps can be performed on the same device. Additionally, the polymer can be blended with one or more additional materials, for example, one or more radio-opaque materials (e.g., tantalum, tantalum oxide, tungsten, bismuth oxide, barium sulfate, platinum, and gold) and/or one or more bioactive materials. In certain embodiments, the injection molding comprises insert molding a metallic wire within the three-dimensional configuration.

In another aspect, the invention includes a vaso-occlusive device produced by any of the methods described herein.

In yet another aspect, the invention includes a vaso-occlusive device comprising at least one polymeric material, wherein said device is formed into and deployed in a three-dimensional configuration. Preferably, the device is formed by injection molding techniques. Furthermore, in preferred embodiments, the vaso-occlusive device comprises at least one absorbable or biodegradable polymer, for example, polyglycolide, poly-L-lactide, poly(g-ethyl glutamates, polyphosphazene, polysaccharides, polyorthoesters, polycaprolactone, polyhydroxybutyrate, polydioxanone, polycarbonates, polyanhydrides, copolymers or blends thereof, collagen, elastin, fibrinogen, fibronectin, vitronectin, laminin, gelatin and combinations thereof. The three-dimensional configuration can be any shape, for example, a cylindrical configuration having a longitudinal axis or a plurality of shaped structures (e.g., ovals, spheres, cones, pyramids, blocks or combinations of these shapes) linked in series.

In any of the devices described herein, the three-dimensional configuration can be a single-molded element or, alternatively, can comprise two or more discrete elements linked together (e.g. end to end). When formed by linking multiple elements, the linking element can be, for example a polymeric wire or a ductile metallic wire. The three-dimensional configuration can further include additional modifications, for example a cylindrical device may include a plurality of channels therein (e.g, channels perpendicular to the longitudinal axis of the device).

In certain embodiments, any of the devices described herein further comprise a severable junction detachably connected to a pusher element. In certain embodiments, the severable junction(s) are, an electrolytically detachable assembly adapted to detach by imposition of a current on said pusher element; a mechanically detachable assembly adapted to detach by movement or pressure imposed on or within said pusher element; a thermally detachable assembly adapted to detach by localized delivery of heat to said junction; a radiation detachable assembly adapted to detach by delivery of electromagnetic radiation to said junction or combinations thereof.

Any of the devices described herein can be further modified, for instance by, micro-machining the injection-molded element; chemically etching the injection-molded element; laser cutting the injection-molded element; and/or linking a plurality of injection-molded elements together (e.g., by soldering, interference fitting, friction fitting, stringing, ultrasonic welding, thermal welding and solvent bonding). A single device may include one or more of such modifications. Additionally, the device may include one or more additional materials, for example, one or more radio-opaque materials (e.g., tantalum, tantalum oxide, tungsten, bismuth oxide, barium sulfate, platinum, and gold) and/or bioactive materials. In certain embodiments, the injection molding comprises insert molding a metallic wire within the three-dimensional configuration.

These and other embodiments of the subject invention will readily occur to those of skill in the art in light of the disclosure herein.

DESCRIPTION OF THE INVENTION

Figure 1:
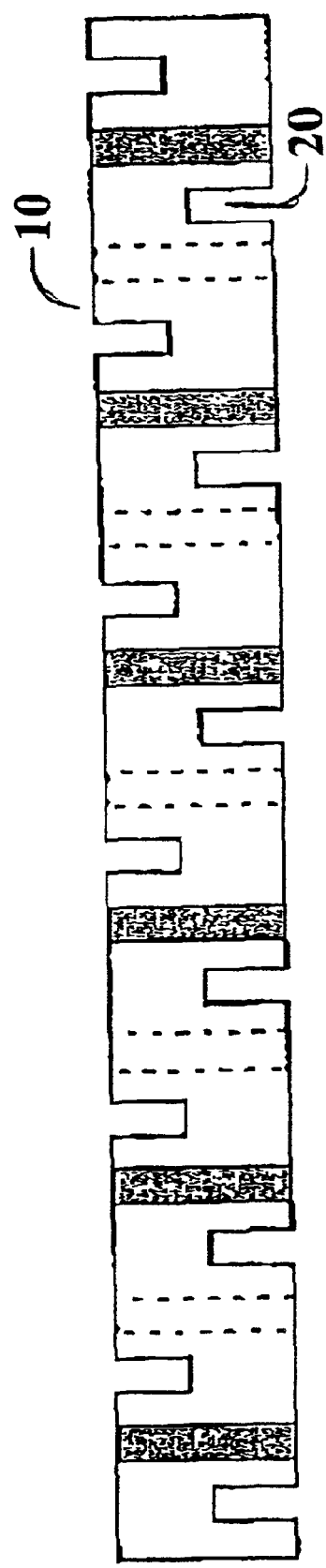
FIG. 1 depicts an exemplary single-molded vaso-occlusive device having a generally tubular and linear configuration with channels spaced along the length of the device.

Occlusive (e.g., embolic) compositions are described. The compositions described herein find use in vascular and neurovascular indications and are particularly useful in treating aneurysms, for example small-diameter, curved or otherwise difficult to access vasculature, for example cerebral aneurysms. Methods of making and using these vaso-occlusive elements are also form aspects of this invention. The compositions and methods described herein are particularly useful when the element is comprised primarily or entirely of polymeric material, for example, absorbable polymeric material.

Advantages of the present invention include, but are not limited to, (i) production of polymeric non-coil elements; (ii) production of polymeric (e.g., partially or fully absorbable vaso-occlusive devices) without the need for winding and/or heat-setting which may be technically difficult; (iii) reducing or eliminating variation (e.g., diameter, strength, etc.) of polymeric vaso-occlusive elements; and (iv) cost-effective production of polymeric elements, for example by use of automation.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to "a polymer" includes a mixture of two or more such polymers and the like.

Thus, described herein are novel injection-molded vaso-occlusive elements and novel methods of manufacturing these elements. Unlike previously described polymeric vaso-occlusive elements, the devices described herein do not have a primary helical geometry (i.e. are not made in a two-step process of helically winding a wire into a coil and then winding the coil into a three-dimensional shape). Rather, the claimed elements are not helically wound and are produced by injection molding, reaction injection molding, extrusion or the like. Further, unlike known vaso-occlusive elements which assume a secondary configuration (e.g., three-dimensional configuration) after extrusion from the deployment catheter, the injection-molded elements described herein typically are formed into their three-dimensional configurations prior to deployment and are delivered and deployed in these secondary configurations. Additionally, unlike most non-injection molded polymeric devices, the cross-sectional configurations of certain embodiments of the injection-molded devices described herein typically vary along the length of the device. In other words, in contrast to regularly wound helical coils, many of the injection molded devices will not have a continuous cross-section along the longitudinal axis.

As used herein the term "injection molded" refers broadly to any technique for forming polymers into desired configurations including extrusion, molding, insert molding, reaction molding and the like. Such techniques are known in the art. Furthermore, micro-machining techniques (e.g., laser or other micro-machining) can also be employed in the manufacture of the vaso-occlusive devices described herein, for example to create holes and/or channels in the molded material.

Thus, in certain embodiments, the vaso-occlusive elements described herein are formed using a mold. The design of molds for injections, runners (hot and cold), gates, vents, cavity layout, and ejection systems is also within the purview of the skilled artisan in view of the teachings herein which, for the first time, apply injection molding techniques to the manufacture and use of vaso-occlusive devices. The elements produced by injection molding are significantly less prone to variability (e.g., in diameter and/or tensile strength) while maintaining the desired occlusive and/or flexibility characteristics. Suitable molding processes include conventional molding process (where a coolant such as water or oil is circulated through the mold continuously while mold temperature is regulated by a controller such as a thermolator or chiller); pulsed cooling processes (where a manifold is designed to pulse cold water through the system at selected times, for example, once the desired temperature is reached); gas-assisted molding; multi-live feed processes; co-injection and sandwich molding and the like. For a review of injection molding techniques, see, for example, *Medical Device & Diagnostic Industry Magazine*, April 1998 cover story and accompanying articles and columns.

The vaso-occlusive elements of the present invention can be a single-molded element or, alternatively, can be comprised of a plurality of molded elements which are linked to form the desired configuration. FIG. 1 shows one exemplary embodiment of a single-molded element in which the overall cylindrical structure 10 include a plurality of evenly spaced, rectangular channels 20 therein. The channels may be formed during molding or may be formed after molding, for example by micro-machining, laser and/or chemical etching techniques. Shaded areas denote channels facing the view while dotted lines denote channels on the back side of the cylindrical structure. It will be apparent that the channels need not be evenly spaced over the exterior surface of the element and, moreover, that these channels may be of the same or similar shape and/or dimensions or that their dimensions may vary across the longitudinal axis of the device. As shown in FIG. 1, the channels are preferably perpendicular to the longitudinal axis of the device. Alternatively, one or more of the channels may be angled anywhere from 0 to 90° (or any value therebetween) relative to the plane of the longitudinal axis of the device.

Figure 2:
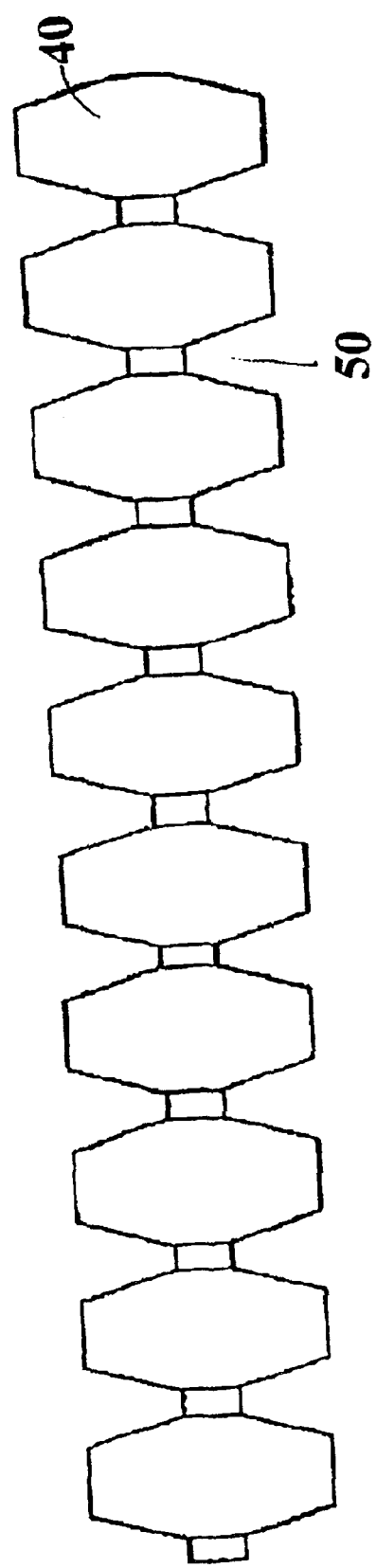
FIG. 2 depicts another exemplary single-molded vaso-occlusive device having a generally configuration of a series of shaped elements linked to one another.

FIG. 2 shows yet another exemplary single-molded element having the appearance of a series of similarly shaped elements 40 linked to one another. In single-molded embodiments as shown in FIG. 2, the linked elements are not separate components. Further, it will be apparent that these linked elements can be virtually any three-dimensional shape, for example, sphere-like, ovoid, conical, pyramidal, disks, blocks (including cubes and blocks with more than 6 sides), and the like. Different shapes and/or sizes can be used in the same vaso-occlusive element. Additionally, the nature of the linking component (e.g., dimension, hollowness, etc.) can vary between different elements.

Figure 3:
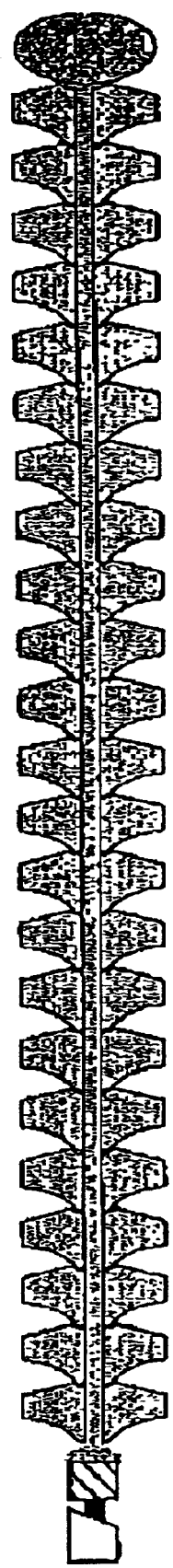
FIG. 3 depicts an exemplary string of molded elements linked together to provide an overall coil-like configuration.
Figure 4:
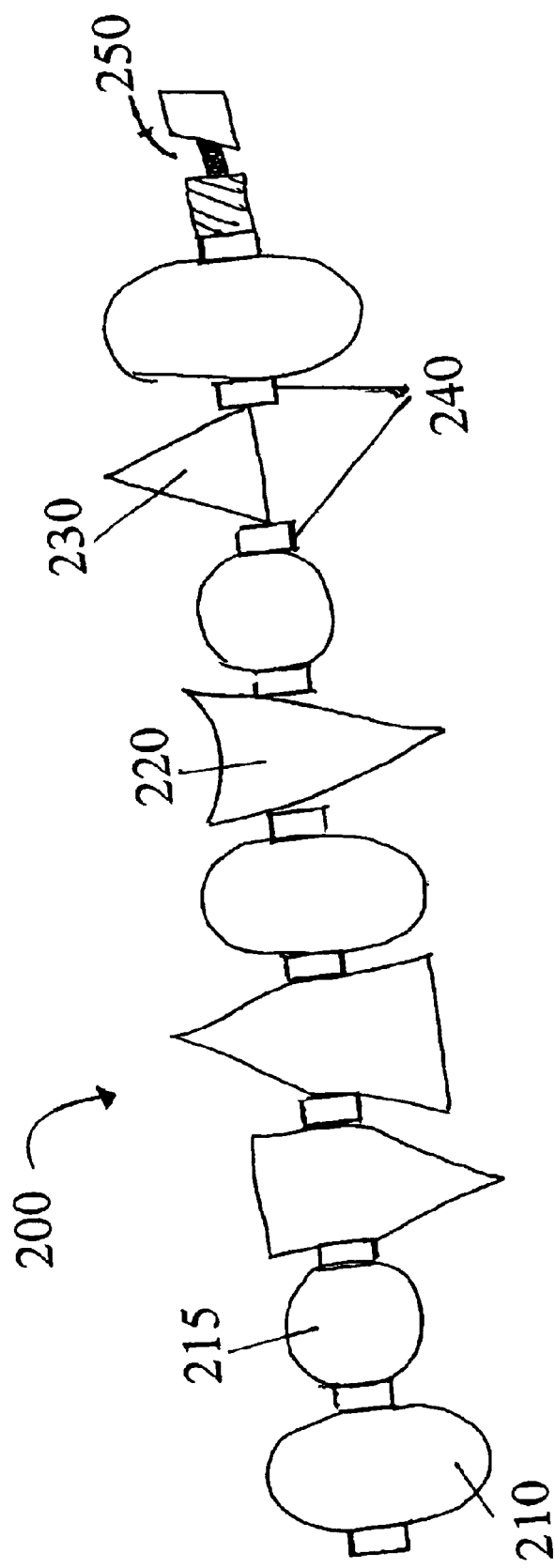
FIG. 4 depicts an exemplary device 200 having a series of shapes elements. Exemplary shapes depicted in the drawing include ovoid 210, spherical 215, conical 220, and pyramidal 230 elements. The series of shaped elements are linked 240 and are detachably connected to a pusher elements 250.

FIG. 3 shows an exemplary embodiment of an injection-molded vaso-occlusive element formed from a plurality of individually molded elements linked together after molding. Like FIG. 2, FIG. 3 shows an embodiment in which the overall appearance of the device is a series of similarly shaped elements linked to each other. Again, the shaped components can be any three-dimensional shape and each individual component can vary in shape and/or dimension.

Thus, the injection-molded vaso-occlusive devices be comprised of a variety of material and may take on a variety of shapes and/or configurations. Braided absorbable vaso-occlusive devices are also included within the scope of the present invention. It is further within the scope of this invention that the vaso-occlusive device comprise shapes or structures other than those shown in the Figures, for examples, spheres, ellipses, spirals, figure-8 shapes, etc. Stretch-resistant configurations can also be designed and manufactured, for example, by including structural features (e.g., lines, channels, etc.) in the mold that impart stretch-resistancy.

Configurations described herein can also be created by micro-machining channels at desired locations of an essentially tube-like structure. It will also be apparent that the vaso-occlusive elements described herein need not be linear and that curves or angles can be introduced into the overall configuration by using suitable molds, post-molding modifications (e.g., heating at a temperature above the glass transition temperature of the polymeric material or plasticizing to achieve desired turns or angles) and/or by providing suitable angled linkages between individual molded elements. These linkages can be provided by any suitable method including, but not limited to, soldering, friction, mechanical interlocks, adhesives, solvent bonding, stringing together, ultrasonic welding, thermal welding and the like.

In one aspect, the injection-molded elements comprise an absorbable polymer suitable in occluding aneurysms. The term "absorbable" refers to any agent which, over time, is no longer identifiable at the site of application in the form it was injected, for example having been removed via degradation, metabolism, dissolving or any passive or active removal procedure. Absorbable vaso-occlusive devices are described in detail in co-owned patent application entitled "Absorbable Implantable Vaso-Occlusive Member," filed even date herewith. In preferred embodiments, the polymer is absorbable, for example, polyglycolide, poly-L-lactide, poly (g-ethyl glutamates, polyphosphazene, polysaccharides, polyorthoesters, polycaprolactone, polyhydroxybutyrate, polydioxanone, polycarbonates, polyanhydrides, copolymers of one of these polymers and/or blends of these polymers. Non-limiting examples of bioabsorbable proteins include synthetic and polysaccharide biodegradable hydrogels, collagen, elastin, fibrinogen, fibronectin, vitronectin, laminin and gelatin. Many of these materials are commercially available. Fibrin-containing compositions are commercially available, for example from Baxter. Collagen containing compositions are commercially available, for example from Cohesion Technologies, Inc., Palo Alto, Calif. Fibrinogen-containing compositions are described, for example, in U.S. Pat. Nos. 6,168,788 and 5,290,552. As will be readily apparent, absorbable materials can be used alone or in any combination with each other and/or other materials.

Furthermore, the injection-molded vaso-occlusive devices of the present invention can also be used in combination with additional components. For example, lubricious materials (e.g., hydrophilic) materials may be used to coat the injection-molded device to help facilitate delivery. One or more bioactive materials may also be included. The term "bioactive" refers to any agent which exhibits effects in vivo, for example a thrombotic agent, a therapeutic agent or the like. Non-limiting examples of bioactive materials include cytokines; extracellular matrix molecules (e.g., collagen); trace metals (e.g., copper); and other molecules that stabilize thrombus formation or inhibit clot lysis (e.g., proteins or functional fragments of proteins, including but not limited to Factor XIII, $\alpha_2$-antiplasmin, plasminogen activator inhibitor-1 (PAI-1) or the like). Non-limiting examples of cytokines which may be used alone or in combination in the practice of the present invention include, basic fibroblast growth factor (bFGF), platelet derived growth factor (PDGF), vascular endothelial growth factor (VEGF), transforming growth factor beta (TGF-$\beta$) and the like. Cytokines, extracellular matrix molecules and thrombus stabilizing molecules (e.g., Factor XIII, PAI-1, etc.) are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additionally, bioactive polypeptides can be synthesized recombinantly as the sequence of many of these molecules are also available, for example, from the GenBank database. Thus, it is intended that the invention include use of DNA or RNA encoding any of the bioactive molecules. Cells (e.g., fibroblasts, stem cells, etc.) can also be included. Such cells may be genetically modified. Furthermore, it is intended, although not always explicitly stated, that molecules having similar biological activity as wild-type or purified cytokines, extracellular matrix molecules and thrombus-stabilizing proteins (e.g., recombinantly produced or mutants thereof) and nucleic acid encoding these molecules are intended to be used within the spirit and scope of the invention. Further, the amount and concentration of liquid embolic and/or other bioactive materials useful in the practice of the invention can be readily determined by a skilled operator and it will be understood that any combination of materials, concentration or dosage can be used, so long as it is not harmful to the subject.

It also may be desirable to include one or more radio-opaque materials for use in visualizing the devices in situ. Thus, the injection-molded devices may be coated or mixed with radio-opaque materials such as metals (e.g. tantalum, gold or platinum particles); barium sulfate; bismuth subcarbonate; or the like.

Methods of making the polymeric vaso-occlusive devices described are also provided. The vaso-occlusive devices described herein are typically formed by injection molding techniques as described above to form a size and shape suitable for fitting snugly within a vascular cavity (e.g., an aneurysm, or perhaps, a fistula).

Methods of Use

The embolic compositions described herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will be such as to be capable of being advanced entirely through the catheter to place injection-molded vaso-occlusive device at the target site but yet with a sufficient portion of the distal end of the delivery mechanism protruding from the distal end of the catheter to enable detachment of the implantable vaso-occlusive device. For use in peripheral or neural surgeries, the delivery mechanism will normally be about 100–200 cm in length, more normally 130–180 cm in length. The diameter of the delivery mechanism is usually in the range of 0.25 to about 0.90 mm. Briefly, the liquid embolics and/or occlusive devices described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g., mechanical devices, injection-molded vaso-occlusive members and/or liquid embolics and bioactive materials) which cause formation of an emboli and, at some later time, is at least partially replaced by neovascularized collagenous material formed around the implanted vaso-occlusive devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the absorbable vaso-occlusive device at the distal end, is advanced through the catheter.

Once the selected site has been reached, the absorbable vaso-occlusive device is extruded, for example by loading onto a pusher wire. Preferably, the vaso-occlusive device is loaded onto the pusher wire via a mechanically or electrolytically cleavable junction (e.g., a GDC-type junction that can be severed by application of heat, electrolysis, electrodynamic activation or other means). Additionally, the vaso-occlusive device can be designed to include multiple detachment points, as described in co-owned U.S. patent application titled "LIGHT-ACTIVATED MULTI-POINT DETACHMENT MECHANISM". They are held in place by gravity, shape, size, volume, magnetic field or combinations thereof.

Modifications of the procedure and vaso-occlusive devices described above, and the methods of using them in keeping with this invention will be apparent to those having skill in this mechanical and surgical art. These variations are intended to be within the scope of the claims that follow.

What is claimed is:

1. A method for producing a vaso-occlusive element for use in occluding a vessel, the method comprising the step of injection molding an absorbable polymeric material into the three-dimensional configuration, wherein the three-dimensional configuration self-forms upon deployment or where the three-dimensional configuration does not change upon deployment into the vessel.

2. The method of claim 1, wherein the absorbable material is selected from the group consisting of polyglycolide, poly-L-lactide, poly(g-ethyl glutamates, polyphosphazene, polysaccharides, polyorthoesters, polycaprolactone, polyhydroxybutyrate, polydioxanone, polycarbonates, polyanhydrides, copolymers or blends thereof, collagen, elastin, fibrinogen, fibronectin, vitronectin, laminin, gelatin and combinations thereof.

3. The method of claim 1, wherein the three-dimensional configuration comprises a cylindrical configuration having a longitudinal axis.

4. The method of claim 3, wherein the cylindrical configuration further includes a plurality of channels therein.

5. The method of claim 4, wherein the channels are perpendicular to the longitudinal axis of the device.

6. The method of claim 1, wherein the three-dimensional configuration comprises a plurality of shaped structures linked in series.

7. The method of claim 6, wherein the shaped elements are ovoid.

8. The method of claim 6, wherein the shaped elements are spherical.

9. The method of claim 6, wherein the shaped elements are conical or pyramidal.

10. The method of claim 6, wherein the three-dimensional configuration is a single-molded element.

11. The method of claim 6, wherein the three-dimensional configuration is formed from two or more separate elements.

12. The method of claim 6, wherein the separate elements are linked by a polymeric wire or a ductile metallic wire.

13. The method of claim 1, further comprising the step of providing one or more severable junctions detachably connected to a pusher element.

14. The method of claim 13, wherein the severable junction comprises an electrolytically detachable assembly adapted to detach by imposition of a current on said pusher element.

15. The method of claim 13, wherein the severable junction comprises a mechanically detachable assembly adapted to detach by movement or pressure imposed on or within said pusher element.

16. The method of claim 13, wherein the severable junction comprises a thermally detachable assembly adapted to detach by localized delivery of heat to said junction.

17. The method of claim 13, wherein the severable junction comprises a radiation detachable assembly adapted to detach by delivery of electromagnetic radiation to said junction.

18. The method of claim 1, further comprising micro-machining the injection-molded element.

19. The method of claim 1, further comprising chemically etching the injection-molded element.

20. The method of claim 1, further comprising laser cutting the injection-molded element.

21. The method of claim 1, further comprising linking a plurality of the injection-molded elements.

22. The method of claim 21, wherein the linking is by a method selected from the group consisting of soldering, interference fitting, friction fitting, stringing, ultrasonic welding, thermal welding and solvent bonding.

23. The method of claim 1, further comprising the step of blending one or more radio-opaque materials with the polymer.

24. The method of claim 1, wherein the injection molding comprises insert molding a metallic wire within the three-dimensional configuration.

25. A vaso-occlusive device produced by the method of claim 1.

26. A vaso-occlusive device comprising at least one polymeric material, wherein said device is formed into a three-dimensional configuration and is adapted to be deployed into a body cavity in the three-dimensional configuration.

27. The vaso-occlusive device of claim 26, wherein the vaso-occlusive device comprises at least one absorbable or biodegradable polymer.

28. The device of claim 27, wherein the absorbable material is selected from the group consisting of polyglycolide, poly-L-lactide, poly(g-ethyl glutamates, polyphosphazene, polysaccharides, polyorthoesters, polycaprolactone, polyhydroxybutyrate, polydioxanone, polycarbonates, polyanhydrides, copolymers or blends thereof, collagen, elastin, fibrinogen, fibronectin, vitronectin, laminin, gelatin and combinations thereof.

29. The device of claim 26, wherein the three-dimensional configuration comprises a cylindrical configuration having a longitudinal axis.

30. The device of claim 29, wherein the cylindrical configuration further includes a plurality of channels therein.

31. The device of claim 30, wherein the channels are perpendicular to the longitudinal axis of the device.

32. The device of claim 26, wherein the three-dimensional configuration comprises a plurality of shaped structures linked in series.

33. The device of claim 32, wherein the shaped elements are ovoid.

34. The device of claim 32, wherein the shaped elements are spherical.

35. The device of claim 32, wherein the shaped elements are conical or pyramidal.

36. The device of claim 32, wherein the three-dimensional configuration is a single-molded element.

37. The device of claim 32, wherein the three-dimensional configuration is formed from two or more separate elements.

38. The device of claim 32, wherein the separate elements are linked by a polymeric wire or a ductile metallic wire.

39. The device of claim 26, further comprising the step of providing severable junction detachably connected to a pusher element.

40. The device of claim 39, wherein the severable junction comprises an electrolytically detachable assembly adapted to detach by imposition of a current on said pusher element.

41. The device of claim 39, wherein the severable junction comprises a mechanically detachable assembly adapted to detach by movement or pressure imposed on or within said pusher element.

42. The device of claim 39, wherein the severable junction comprises a thermally detachable assembly adapted to detach by localized delivery of heat to said junction.

43. The device of claim 39, wherein the severable junction comprises a radiation detachable assembly adapted to detach by delivery of electromagnetic radiation to said junction.

44. The device of claim 26, further comprising a radio-opaque material.

45. The device of claim 44, where the radio-opaque material is selected from the group consisting of tantalum, tantalum oxide, tungsten, bismuth oxide, barium sulfate, platinum, and gold.

46. The device of claim 26, further comprising a bioactive material.

47. The device of claim 26, produced by injection molding.

48. The device of claim 47, wherein the device is micro-machined.

* * * * *